United States Patent [19]

Turner

[11] Patent Number: 5,422,021

[45] Date of Patent: Jun. 6, 1995

[54] FABRIC SOFTENING

[75] Inventor: Graham A. Turner, Merseyside, England

[73] Assignee: Lever Brothers Company, Division of Conopco, Inc., New York, N.Y.

[21] Appl. No.: 195,594

[22] Filed: Feb. 14, 1994

Related U.S. Application Data

[63] Continuation of Ser. No. 890,333, May 26, 1992, abandoned, which is a continuation of Ser. No. 580,890, Sep. 11, 1990, abandoned.

[30] Foreign Application Priority Data

Sep. 19, 1989 [GB] United Kingdom ............... 8921168

[51] Int. Cl.$^6$ ............................................. D06M 13/46
[52] U.S. Cl. ................................. 252/8.8; 252/8.6; 252/541; 252/544; 252/546; 252/547; 554/110; 564/291; 564/296
[58] Field of Search ............... 252/8.6, 8.8, 541, 544, 252/546, 547; 554/110; 564/291, 296

[56] References Cited

U.S. PATENT DOCUMENTS

| | | |
|---|---|---|
| 3,872,138 | 3/1975 | Ogata ............................. 252/8.8 |
| 3,915,867 | 10/1975 | Kang et al. ..................... 252/8.8 |
| 4,137,180 | 1/1979 | Naik et al. ..................... 252/8.8 |
| 4,308,024 | 12/1981 | Wells ................................ 8/137 |
| 4,429,859 | 2/1984 | Steiner et al. ................ 252/8.8 |
| 4,767,547 | 8/1988 | Straathof et al. ............. 252/8.8 |
| 4,830,771 | 5/1989 | Ruback et al. ................ 252/8.8 |
| 4,963,274 | 10/1990 | Ruback et al. ............... 252/8.75 |
| 4,965,100 | 10/1990 | Leigh et al. ................... 252/8.8 |
| 5,288,417 | 2/1994 | Bauer et al. ................... 252/8.8 |

Primary Examiner—Paul Liberman
Assistant Examiner—Michael P. Tierney
Attorney, Agent, or Firm—A. Kate Huffman

[57] ABSTRACT

A method of preparing a fabric softening material which comprises a quaternary ammonium material and at least on $C_{8-28}$ alkyl or alkenyl group connected to the molecule via an ester linkage, said method comprising the step of reacting a base material with an alkyl or alkenyl group containing material, such that at least one alkyl or alkenyl group is connected to the base material via an ester linkage, wherein the reaction between the base material and the alkyl or alkenyl group containing material is carried out in the presence of an excess of alkyl or alkenyl groups, said excess being effective to lower the pour point of the softener material.

3 Claims, No Drawings

FABRIC SOFTENING

This is a continuation application of Ser. No. 07/890,333, filed May 26, 1992, now abandoned which is a continuation of Ser. No. 580,890, filed Sep. 11, 1990, now abandoned.

The present invention relates to a method of preparing a fabric softening material, in particular to a method of preparing a softening material comprising one or more $C_8$–$C_{28}$ alkyl or alkenyl groups which are connected to the softener molecule via an ester linkage.

It has been proposed in EP 239 910 corresponding to U.S. Pat. No. 4,767,547 (PROCTER & GAMBLE) to incorporate ester linked quaternary ammonium compounds in fabric softening compositions. U.S. Pat. No. 3,915,867 (STEPAN) discloses the use of N-methyl,N,N-di(beta-$C_{14-18}$ acyloxyethyl) N-beta-hydroxy ethyl ammonium methosulphate in softening compositions. Other ester linked softener materials are described in U.S. Pat. No. 4,137,180 (LEVER BROTHERS). Softener materials comprising ester linkages are especially preferred for use in fabric conditioning compositions for environmental reasons.

A problem with softener materials comprising ester linkages is that they tend to have a relatively high pour point. Pour point can be defined as the lowest temperature at which a material can be observed to flow under specified conditions. (As explained in The Analysis of Fats and Oils by V C Mehlenbacher, The Garrard Press, Champaign, Ill. 1960). A high pour point renders the softener materials sometimes difficult to process. For example, the softener materials as described in U.S. Pat. No. 4,137,180 (LEVER BROTHERS) have high pour points meaning that they are hardly pumpable at ambient temperature and are difficult to disperse in water.

It is an object of the present invention to solve the above mentioned problem and to provide a process for the preparation of ester linked softener materials.

In the preparation of ester linked softener materials it is known to use a base material, which is similar to the final softener molecule, excepting that it does not comprise the alkyl or alkenyl groups connected to the molecule via an ester linkage. This base material is then reacted with one or more alkyl or alkenyl group containing materials, such that one or more alkyl or alkenyl groups become attached to the base material via an ester-linkage. Finally the material may optionally be subjected to further processing steps, for example quaternisation or neutralisation, to form the end-product.

For example in U.S. Pat. No. 3,915,867 (STEPAN) a process for the preparation of an ester-linked quaternary ammonium material is disclosed, wherein triethanolamine as the base material in the presence of a sodium methoxide solution is reacted with a fatty acid methyl ester mixture in an esterification reaction to form a molecule wherein two alkyl chains are connected to the base molecule via an ester linkage. The molar ratio of fatty acid methyl ester to triethanolamine is 2:1.

In U.S. Pat. No. 4,137,180 (LEVER BROTHERS) a similar method of preparation is disclosed, wherein di-methyl-amino-propan 1,2-diol as the base material is reacted with tallow fatty acids in an esterification reaction to form a molecule, wherein two alkyl groups are connected to the base molecule via an ester link. The molar ratio of tallow fatty acid to base material is typically 2.2:1. The obtained material is made into the final product by quaternisation in the presence of methyl chloride. An alternative method of preparation is disclosed wherein glycidyl trimethyl ammonium chloride as the base material is reacted with tallow fatty acid anhydride to form a mixture of monoester and diester quaternary ammonium salt in a weight ratio of 3:1 diester to monoester.

It has now been found, that the pour point of the obtained materials can markedly be reduced when the reaction of the base-material with the alkyl or alkenyl containing material is carried out in the presence of an excess of alkyl or alkenyl group containing material.

The alkyl or alkenyl group containing material is in excess when the number of moles of alkyl or alkenyl group containing material is greater than the number of moles of the base material multiplied by the number of sites capable of forming an ester link in the base material. For example in U.S. Pat. No. 4,137,180 a base material is di-methyl-amino-propane 1,2 diol which has two sites capable of forming an ester link. Molar ratios of alkyl or alkenyl group containing material to base material greater than 2:1 are thus in excess for this base material.

Accordingly, the present invention provides a method of preparing a softening material which comprises a quaternary ammonium group comprising the step of reacting a base material with an alkyl or alkenyl group containing material such that at least one alkyl or alkenyl group is connected to the base material via an ester linkage wherein the reaction takes place in the presence of more than a 10 mole % excess of the alkyl or alkenyl group containing material said excess being effective to lower the pour point of the softening material and wherein the softening material has a weight ratio of diester material to monoester material greater than 3:1.

Preferably the reaction is carried out such that two $C_{8-28}$ alkyl or alkenyl groups are attached to the base-material via an ester linkage. Most preferably the method of the invention is used to prepare softener material of the formula:

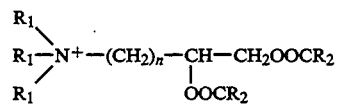

wherein each $R_1$ group is independently selected from $C_{1-4}$ alkyl, hydroxyalkyl groups containing from one to four carbon atoms, or a benzyl group; and each $R_2$ groups is independently selected from $C_{8-28}$ alkyl or alkenyl groups; n is an integer from 0–5. A suitable base material for preparing these materials is a tertiary amine comprising two $R_1$ groups and one 1,2 diol-group connected to the nitrogen atom via the $(CH_2)_n$ group.

The reaction between the base material and the alkyl or alkenyl group containing material will result in the formation of one or more ester linkages in the molecule, therefore the base material and the alkyl or alkenyl group containing material for reaction with the base material in combination must be able to form ester linkages. Preferably the base-material comprises one or more hydroxy groups for reaction with the alkyl or alkenyl containing materials. The alkyl or alkenyl group containing materials, preferably are fatty acids, their soaps or their $C_{1-6}$ esters. Most preferably the base material comprises two hydroxy groups which react with two free fatty acid molecules to form two ester linkages.

According to the method of the invention the esterification reaction is carried out in the presence of a greater than 10 mole % excess of alkyl or alkenyl groups based on the number of moles of alkyl or alkenyl group containing material. Preferably the amount of alkyl or alkenyl group containing material in excess of the reacting alkyl or alkenyl group containing material is more than 20 mole %, more preferred the excess is more than 50 mole %, preferably between 100 and 500 mole %, most preferred between 200 and 400 mole %.

The excess of alkyl or alkenyl groups may come from any source, although the following type of alkyl or alkenyl group containing materials are preferred: $C_{8-28}$ fatty acids, alcohols, ketones, esters or mixtures thereof.

Preferably the excess of alkyl or alkenyl group containing materials is the same material as the alkyl or alkenyl material used for reacting with the base-material. For example in the preparation of softener materials according to U.S. Pat. No. 4,137,180 (LEVER BROTHERS) the base material is reacted with a free fatty acid. For modifying this process according to the invention the reaction between the base material and the free fatty acid is carried out in the presence of an excess of materials which contain alkyl or alkenyl groups. This excess material may be selected from any alkyl or alkenyl groups containing materials such as the above mentioned $C_{8-28}$ fatty acids, alcohols, ketones, esters or mixtures thereof, preferably however the excess of alkyl or alkenyl groups comes from an excess of fatty acid materials.

Therefore a preferred method of preparing softener materials according to the invention involves the reaction of the base-material with a fatty acid, a soap thereof or a $C_{1-6}$ ester thereof, wherein an excess of the fatty acid, its soap or its $C_{1-6}$ ester is present.

The softening material resulting from the method of the invention may comprise a mixture of monoesters, diesters, triesters etc. depending on the base material. According to the method of the present invention the weight ratio of diester to monoester in the softening material is greater than 3:1 since the diester materials provide a greater fabric softening effect than the equivalent monoester. Preferably the weight ratio of diester to monoester is greater than 4:1, more preferably greater than 25:1.

The product obtained after reacting the base-material with the ester-forming alkyl or alkenyl group containing materials, optionally followed by one or more further reaction steps, which do not substantially change the ratio of ester linked material to excess material, such as for example neutralisation or quaternisation, is a homogeneous mixture of the desired ester-linked softener material and the excess of alkyl or alkenyl groups containing materials. This mixture has a lower pour point than the corresponding mixture in the absence of the excess material. Furthermore the in-situ preparation of the homogeneous mixture according to the invention is clearly preferred over the separate preparation of a mixture of ester-linked materials and excess material, because the latter process requires an additional processing step and often does not give the desired homogeneity of the mixture.

Preferably the pour point of the softening material obtained by a method according to the invention is less than 75° C. more preferred less than 65° C. especially preferred less than 60° C.

Softening materials obtained by a method according to the invention may be used for the preparation of fabric conditioning compositions, for example for the preparation of liquid rinse conditioning products comprising an aqueous base wherein the softening materials are dispersed. Also substrates impregnated with the softening materials may advantageously be used for laundry drier purposes.

The invention will be illustrated by means of the following example:

EXAMPLE I

Softener materials according to formula I were prepared in line with Example I of U.S. Pat. No. 4,137,180 as follows:

Compound A (di-methyl-amino-propan 1,2-diol) was reacted with varying amounts of tallow fatty acids by mixing the ingredients and heating the mixture for 7 hours at 120° C., followed by heating for 15 hours under vacuum at 185° C. The reaction conditions and the further process was as described in U.S. Pat. No. 4,137,180 example I.

The following amounts (in grams) of Compound A to fatty acid were used:

|  | COMPOUND A | FATTY ACID | Molar Ratio Fatty Acid:A | % (Mole) Excess Fatty Acid |
|---|---|---|---|---|
| CONTROL* | 34.5 | 175 | 2.2:1 | 10 |
| Example 1 | 34.5 | 180 | 2.26:1 | 13 |
| Example 2 | 34.5 | 185 | 2.34:1 | 17 |
| Example 3 | 34.5 | 190 | 2.38:1 | 19 |
| Example 4 | 34.5 | 195 | 2.45:1 | 22.5 |
| Example 5 | 34.5 | 200 | 2.51:1 | 25.5 |
| Example 6 | 34.5 | 210 | 2.63:1 | 31.5 |
| Example 7 | 34.5 | 220 | 2.76:1 | 38 |
| Example 8 | 34.5 | 235 | 2.95:1 | 47.5 |
| Example 9 | 34.5 | 350 | 3.13:1 | 56.5 |
| Example 10 | 34.5 | 300 | 3.76:1 | 88 |
| Example 11 | 34.5 | 400 | 5.02:1 | 151 |
| Example 12 | 34.5 | 500 | 6.27:1 | 213.5 |
| Example 13 | 34.5 | 175 | 2.2:1 | 10 |
| Example 14 | 34.5 | 165 | 2.07:1 | 3.5 |

*followed by a recrystallisation step as described in U.S. Pat. No. 4 137 180, this recrystallisation step is not carried out in the remaining examples.

I claim:

1. A method of preparing a softening material including a quaternary ammonium group comprising:
   (a) selecting a base material comprising a tertiary amine having two $R_1$ groups, each $R_1$ group independently selected from $C_{1-4}$ alkyl, alkenyl or hydroxy alkenyl groups and one 1,2 diol group connected to the nitrogen atom via a $(CH_2)_n$ group;
   (b) selecting an alkyl or alkenyl group containing material in a quantity of more than 100 mole percentage excess of the base material, the material selected from the group consisting of $C_8$–$C_{28}$ monobase fatty acids, and mixtures thereof;
   (c) esterifying the base material with the alkyl or alkenyl group-containing material; and
   (d) quaternizing the product of step (c) to form a softening material of formula

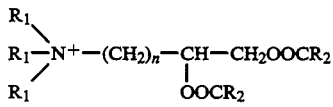

wherein each $R_1$ group is independently selected from $C_{1-4}$ alkyl, alkenyl or hydroxyalkyl groups; and each $R_2$ group is independently selected from $C_{8-28}$ alkyl or alkenyl groups; and n is an integer from 0 to 5, the softening material having a pour point of less than 75° C. and a weight ratio of diester material to monoester material greater than 3:1, with the provision that the softening material is not recrystallized.

2. The method according to claim 1 wherein the step of selecting the alkyl or alkenyl group containing material comprises selecting more than a 200 mole percentage excess of the alkyl or alkenyl group containing material.

3. The method according to claim 1 wherein the esterifying step comprises forming the softening material having a weight ratio of diester material to monoester material of greater than 4:1.

* * * * *